United States Patent
Hilliard, Jr. et al.

(10) Patent No.: US 11,147,755 B2
(45) Date of Patent: Oct. 19, 2021

(54) ALUMINUM-FREE ANTIPERSPIRANT / DEODORANT COMPOSITIONS

(71) Applicant: Colgate-Palmolive Company, New York, NY (US)

(72) Inventors: Peter Hilliard, Jr., Far Hills, NJ (US); Sharon Kennedy, Randallstown, MD (US); Darrick Carlone, New Vernon, NJ (US); Cristina Bielli, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 50 days.

(21) Appl. No.: 16/468,778

(22) PCT Filed: Dec. 8, 2017

(86) PCT No.: PCT/US2017/065223
§ 371 (c)(1),
(2) Date: Jun. 12, 2019

(87) PCT Pub. No.: WO2018/111705
PCT Pub. Date: Jun. 21, 2018

(65) Prior Publication Data
US 2019/0358134 A1   Nov. 28, 2019

Related U.S. Application Data

(60) Provisional application No. 62/434,223, filed on Dec. 14, 2016.

(51) Int. Cl.
| | |
|---|---|
| A61K 8/25 | (2006.01) |
| A61K 8/02 | (2006.01) |
| A61K 8/04 | (2006.01) |
| A61K 8/34 | (2006.01) |
| A61K 8/36 | (2006.01) |
| A61K 8/81 | (2006.01) |
| A61Q 15/00 | (2006.01) |

(52) U.S. Cl.
CPC .............. *A61K 8/25* (2013.01); *A61K 8/0229* (2013.01); *A61K 8/042* (2013.01); *A61K 8/345* (2013.01); *A61K 8/361* (2013.01); *A61K 8/8176* (2013.01); *A61Q 15/00* (2013.01); *A61K 2800/30* (2013.01); *A61K 2800/48* (2013.01)

(58) Field of Classification Search
CPC .... A61K 8/25; A61K 8/8176; A61K 2800/48; A61K 2800/30; A61Q 15/00
See application file for complete search history.

(56) References Cited

U.S. PATENT DOCUMENTS

| | | |
|---|---|---|
| 5,508,024 A | 4/1996 | Tranner |
| 6,174,521 B1 | 1/2001 | Li et al. |
| 6,558,710 B1 | 5/2003 | Godfrey |
| 7,189,387 B2 | 3/2007 | Chuah et al. |
| 7,976,828 B2 | 7/2011 | Popoff et al. |
| 9,707,171 B2 | 7/2017 | Fan et al. |
| 9,750,670 B2 | 9/2017 | Pan et al. |
| 9,757,316 B2 | 9/2017 | Pan et al. |
| 9,795,810 B2 | 10/2017 | Gale |
| 9,827,177 B2 | 11/2017 | Yuan et al. |
| 2003/0206973 A1 | 11/2003 | Gale |
| 2004/0022750 A1 | 2/2004 | Lee |
| 2005/0249763 A1* | 11/2005 | Legendre ............. A61Q 19/008 424/401 |
| 2006/0008434 A1 | 1/2006 | Knopf et al. |
| 2007/0025942 A1 | 2/2007 | Kutylowski |
| 2008/0233067 A1 | 9/2008 | Lee |
| 2010/0104612 A1* | 4/2010 | Cropper .................. A61K 8/33 424/401 |
| 2012/0114582 A1 | 5/2012 | Batchelor et al. |
| 2013/0131188 A1* | 5/2013 | Beckedahl ............... A61K 8/33 514/772 |
| 2015/0118173 A1 | 4/2015 | Farwick et al. |
| 2016/0089321 A1 | 3/2016 | Anconi et al. |
| 2016/0235637 A1* | 8/2016 | Britze ...................... A61K 8/34 |

FOREIGN PATENT DOCUMENTS

| | | |
|---|---|---|
| CN | 1261265 | 7/2000 |
| CN | 1791379 | 6/2006 |
| CN | 105232361 | 1/2016 |
| RU | 2003101327 | 5/2004 |
| RU | 2436563 | 12/2011 |
| WO | 1993/24105 | 12/1993 |
| WO | 2013/052454 | 4/2013 |
| WO | 2016/030048 | 3/2016 |

OTHER PUBLICATIONS

International Search Report and Written Opinion of the International Searching Authority in International Application No. PCT/US2017/065223, dated Mar. 29, 2018.

* cited by examiner

Primary Examiner — Andrew S Rosenthal

(57) ABSTRACT

An antiperspirant/deodorant composition in the form of stick, cream, or flowable gel may include a carrier that may include a polyhydric alcohol or a mixture of a polyhydric alcohol and water; a thickening agent including a $C_{14-22}$ fatty acid salt; and an antiperspirant active dispersed in the carrier. The antiperspirant active may include a layered silicate clay and/or an acyl substituted polyvinylpyrrolidone. The antiperspirant/deodorant composition may be primarily free of a $C_{1-5}$ monohydric alcohol and a metal salt based antiperspirant active, such as aluminum-based antiperspirant active.

11 Claims, No Drawings

ALUMINUM-FREE ANTIPERSPIRANT / DEODORANT COMPOSITIONS

BACKGROUND

Antiperspirant/deodorant compositions are used to reduce the perspiration in an axillary (underarm) region and/or to kill bacteria in this region to reduce or eliminate body odor caused by bacterial growth in this region. Antiperspirants/deodorants can be provided in many forms, such as a roll on, a gel, or as a solid stick. Stick antiperspirant/deodorant applicators are essentially made of a solid or semi-solid material (i.e., a base composition that is firm to the touch) impregnated with ingredients that function to reduce perspiration, kill bacteria or limit their growth by reducing the moist climate in which bacteria thrive, fragrances, stabilizers, moisturizers, etc. To use the stick applicator, the user swipes the stick applicator in the armpit one or more times thereby coating the underarm with a thin layer of the antiperspirant/deodorant material. As would be expected, there are characteristics that make some carrier materials superior to others. For example, product hardness, moisture content, stickiness, oiliness, wetness, ease by which the antiperspirant/deodorant material goes on to the underarm (payout) and ease of application (e.g., how much pressure does the user have to use to deposit the required amount of deodorant material to the underarm referred to herein as "glide"), the ability of the deodorant material to stay on the underarm skin and hair and resist coming off (retention), visibility of deodorant residue on skin and clothing (visible residue), staining of clothing, irritation and inflammation of the skin, flow resistant to body heat (i.e., the deodorant composition material does not "drip" or "run" appreciably after application), etc.

Various metallic salts, for example, of zinc, iron and aluminum have been used as antiperspirant actives, with chlorohydrates and chlorides of aluminum, and aluminum and zirconium being the most commonly used antiperspirant active. However, there is a growing trend to replace these salts with other active metal salts. Zinc which has antibacterial properties has been explored as a possible candidate to replace aluminum. However, Phinney in U.S. Pat. No. 5,512,274 reported that zinc salts precipitate as hydroxides in the range of pH of 6.5 to 8.0, and have been shown to behave erratically, being effective as an antiperspirant only for very irregular periods of time, which makes them undependable. The sporadic efficacy of zinc salts was speculated to be due to various factors, such as lack of hydrolysis conversion to relatively inactive carbonate or oxide, or some other factors or combination of factors.

Furthermore, Yuan and Pan in US patent publication no. 2015/0313821 reported that zinc oxide is weakly soluble at low pH. However, due to human perspiration having a pH of 5-6, the perspiration can reduce the levels of precipitation of the zinc oxide compared to precipitation levels at neutral pH. Moreover, the perspiration can gradually dissolve the depositions, reducing the duration of action of the formulation containing zinc.

Hence, there remains a desire for new antiperspirant/deodorant compositions in the form of stick, cream, or flowable gel that are free of metal salt-based antiperspirant actives.

BRIEF SUMMARY

Disclosed herein is an antiperspirant/deodorant composition including a carrier, a thickening agent, and an antiperspirant active. The carrier may include a mixture of a polyhydric alcohol and/or water. The polyhydric alcohol may include an organic compound containing 2 to 6 carbon atoms and 2 to 6 hydroxy groups. The thickening agent may include $C_{14-22}$ fatty acid salt. The $C_{14-22}$ fatty acid salt may include at least one of an alkali metal, an alkaline earth metal, a transition metal, or an amine salt of $C_{14-22}$ fatty acid. The antiperspirant active may include or consist essentially of one or more of a layered silicate clay and an acyl substituted polyvinylpyrrolidone having an acyl chain length ranging from 16 to 30 carbon atoms. The antiperspirant/deodorant composition may be free or essentially free of a $C_{1-5}$ monohydric alcohol.

In an embodiment of the antiperspirant/deodorant composition, the layered silicate clay may include one or more of a sodium calcium aluminum magnesium silicate clay, a lithium magnesium sodium silicate clay, a sodium magnesium fluorosilicate clay, and an organo-modified hectorite clay.

In another embodiment of the antiperspirant/deodorant composition, the $C_{14-22}$ fatty acid salt may include at least one of myristic, palmitic, stearic, behenic, oleic, linoleic, and linolenic acid, and one or more of sodium, potassium, calcium, magnesium, zinc, diethylamine, triethyl amine as a counterion.

In yet another embodiment of the antiperspirant/deodorant composition, the $C_{14-22}$ fatty acid salt may include a completely or a partially neutralized stearic acid.

In one embodiment of the antiperspirant/deodorant composition, the acyl substituted polyvinylpyrrolidone may include the acyl chain length of 30 carbon atoms.

In an embodiment of the antiperspirant/deodorant composition, the polyhydric alcohol may be propylene glycol.

In another embodiment of the antiperspirant/deodorant composition, the polyhydric alcohol may be present in an amount of 65 to 95 weight %, based on the total weight of the antiperspirant/deodorant composition.

In an embodiment of the antiperspirant/deodorant composition, water may be present in an amount of 0.1 to 20 weight %, based on the total weight of the antiperspirant/deodorant composition.

In another embodiment of the antiperspirant/deodorant composition, the $C_{14-22}$ fatty acid salt may be present in an amount of 0.5 to 8 weight %, based on the total weight of the antiperspirant/deodorant composition.

In one embodiment of the antiperspirant/deodorant composition, the antiperspirant active may include clay present in an amount of 0.5 to 5 weight %, based on the total weight of the antiperspirant/deodorant composition.

In an embodiment of the antiperspirant/deodorant composition, the antiperspirant/deodorant composition may be an antiperspirant/deodorant stick composition, an antiperspirant/deodorant cream composition, or an antiperspirant/deodorant flowable gel composition.

In an aspect, a method of reducing apparent perspiration is provided. The method may include providing an antiperspirant/deodorant composition including a carrier, a thickening agent, and an antiperspirant active, and applying the antiperspirant/deodorant composition to an axillary area of a person. The carrier may include a mixture of a polyhydric alcohol and water, wherein the polyhydric alcohol may include an organic compound containing 2 to 6 carbon atoms and 2 to 6 hydroxy groups. The thickening agent may include a $C_{14-22}$ fatty acid salt, wherein the $C_{14-22}$ fatty acid salt may include at least one of an alkali metal, an alkaline earth metal, a transition metal, or an amine salt of $C_{14-22}$ fatty acid. The antiperspirant active may include or consist essentially of one or more of a layered silicate clay and an acyl substituted polyvinylpyrrolidone having an acyl chain length ranging from 16 to 30 carbon atoms. The the antiperspirant/deodorant composition may be essentially free of a $C_{1-5}$ monohydric alcohol. The antiperspirant active in combination with the $C_{14-22}$ fatty acid salt may form a hydrophobic film on the axillary area of the person, thereby acting as moisture barrier and reducing apparent perspiration.

In an embodiment of the method of reducing apparent perspiration, the antiperspirant active may include or consist essentially of both the layered silicate clay and the acyl substituted polyvinylpyrrolidone, and wherein the $C_{14-22}$ fatty acid salt may include a completely or a partially neutralized stearic acid.

In an aspect, there may be a use of a combination of an antiperspirant active and a $C_{14-22}$ fatty acid salt to reduce apparent perspiration when applied to an axillary area of an armpit, wherein the antiperspirant active may include or consist essentially of one or more of a layered silicate clay and an acyl substituted polyvinylpyrrolidone having an acyl chain length ranging from 16 to 30 carbon atoms, wherein the combination of an antiperspirant active and a fatty acid salt may be present in an antiperspirant/deodorant composition including a mixture of a polyhydric alcohol and water, wherein the $C_{14-22}$ fatty acid salt may include at least one of an alkali metal, an alkaline earth metal, a transition metal, or an amine salt of $C_{14-22}$ fatty acid, wherein the polyhydric alcohol may be selected from one or more of organic compounds containing about 2 to about 6 carbon atoms and about 2 to about 6 hydroxy groups, and wherein the antiperspirant/deodorant composition may be essentially free of $C_{1-5}$ monohydric alcohol selected from the group consisting of ethyl alcohol, isopropyl alcohol, n-propanol, n-butanol, sec-butanol, isobutanol, and pentanol.

Further areas of applicability of the present disclosure will become apparent from the detailed description provided hereinafter. It should be understood that the detailed description and specific examples, while indicating some preferred aspects of the invention, are intended for purposes of illustration only and are not intended to limit the scope of the invention.

DETAILED DESCRIPTION

The following description of various preferred aspect(s) is merely exemplary in nature and is in no way intended to limit the invention, its application, or uses.

As used throughout, ranges are used as shorthand for describing each and every value that is within the range as well as the endpoints. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, the term "antiperspirant/deodorant composition" refers to formulations that provide at least one benefit selected from an antiperspirant benefit and a deodorant benefit.

Compositions

The antiperspirant/deodorant compositions of the present disclosure may be a stick form, cream, or flowable gel. In an aspect, the antiperspirant/deodorant compositions include a carrier that may include a polyhydric alcohol or a mixture of a polyhydric alcohol and water; a thickening agent including a $C_{14-22}$ fatty acid salt; and an antiperspirant active dispersed in the carrier with the antiperspirant active including a layered silicate clay and/or an acyl substituted polyvinylpyrrolidone. The antiperspirant/deodorant compositions of the present disclosure may be essentially free of a $C_{1-5}$ monohydric alcohol and may also be essentially free of a metal salt based antiperspirant active. The antiperspirant effect of the antiperspirant/deodorant compositions of the present disclosure may be provided by the combination of a fatty acid salt and an antiperspirant active that may include a layered silicate clay and/or an acyl substituted polyvinylpyrrolidone. Thus, the antiperspirant/deodorant compositions described in the present disclosure may be primarily free of added metal salt based antiperspirant actives such as added aluminum-based antiperspirant actives.

By the term "essentially free of $C_{1-5}$ monohydric alcohol", it is meant that $C_{1-5}$ alkyl alcohols having one hydroxyl group, such as ethyl alcohol, isopropyl alcohol, n-propanol, n-butanol, sec. butanol, isobutanol, pentanol, and mixtures thereof, may not be added to the antiperspirant/deodorant composition of the present disclosure.

In an embodiment, "essentially free of a $C_{1-5}$ monohydric alcohol and essentially free of an aluminum-based antiperspirant active", it is meant that the antiperspirant/deodorant composition may contain less than 0.1 weight %, less than 0.05 weight %, or less than 0.01 weight %, of a $C_{1-5}$ monohydric alcohol and/or a metal based antiperspirant actives, as described below, or that the antiperspirant/deodorant composition contains no $C_{1-5}$ monohydric alcohol and no aluminum-based antiperspirant active.

By the term "essentially free of added aluminum-based antiperspirant actives,", it is meant that aluminum-based antiperspirant actives, may not be added to the antiperspirant/deodorant composition in an amount that could display some antiperspirant/deodorant effect. However, aluminum-based antiperspirant actives may be present in small or trace amounts due to contamination from other ingredients used in the making of the antiperspirant/deodorant formulations of the present disclosure.

In various embodiments of the antiperspirant and/or deodorant compositions described herein, "essentially free of aluminum-based antiperspirant actives" means that the antiperspirant &/or deodorant compositions of the present disclosure contains less than 0.05 weight %, or less than 0.01 weight % of one or more of aluminum-based antiperspirant actives.

As used herein, the term "aluminum-free" means that the composition does not contain any aluminum-based antiperspirant. Non-limiting examples of aluminum-based antiperspirant actives, include those listed in US antiperspirant monograph, such as, for example, aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. However, as used herein, the antiperspirant/deodorant composition that is "aluminum-free" may contain aluminum present in a form that cannot be easily dissolved or leach out, such as, for example, bentonite clays containing aluminum. The aluminum in the aluminum containing clays, such as bentonite clays may be in a totally different form than that present in a typical aluminum-based antiperspirant salts, as defined by the US antiperspirant monograph and astringents such as aluminum sulphate.

The pH of the antiperspirant/deodorant composition of the present disclosure can be in the range of 7 to 11 or 8 to 10 or 8.5 to 10 or 9 to 10.

Antiperspirant Active

In an embodiment of the antiperspirant/deodorant compositions of the present disclosure, the antiperspirant active may include a layered silicate clay and/or an acyl substituted polyvinylpyrrolidone having an acyl chain length ranging from 16 to 30 carbon atoms. In one embodiment, the antiperspirant active may include only an acyl substituted polyvinylpyrrolidone having an acyl chain length ranging from 16 to 30 carbon atoms. In another embodiment, the antiperspirant active may only include a layered silicate clay. In yet another embodiment, the antiperspirant active may include both a layered silicate clay and an acyl substituted polyvinylpyrrolidone having an acyl chain length ranging from 16 to 30 carbon atoms.

Any suitable natural or synthetic layered silicate clay may be used, including hectorites which may be aluminum free clays and bentonites which may be aluminum containing clays. A bentonite clay, may be primarily composted of montmorillonite having the formula $(Na,Ca)_{0.33}(Al, Mg)_2 (Si_4O_{10})(OH)_2 \cdot nH_2O$. Suitable examples of bentonite clay include, but are not limited to, Gelwhite H—sodium calcium aluminum magnesium silicate hydroxide, available from BYK Additives and Instruments, Inc and Vegegum HS—magnesium aluminum silicate, available from Vanderbilt Minerals LLC. A Hectorite clay may be a magnesium based clay, e.g., typically having an approximate chemical composition of $Na_{0.3}(Mg,Li)_3Si4O_{10}(OH)_2$. Suitable examples of the synthetic hectorite clay include, but are not limited to, Laponite XLS, Laponite XLG—lithium magnesium sodium silicate having the formula $Na^+_{0.7}[(Si_8Mg_{5.5}Li_{0.3})O_{20} (OH)_4]^{-0.7}$, Laponite XL21—sodium magnesium fluorosilicate having the formula $Na^+_{10}Mg^{+2}_{16}(Si_4O_{10})^{-4}_6(SiO_2) F^-_{18}$, commercially available from BYK Additives and Instruments, Inc. Examples of organo-modified clays, such as organo-modified hectorite, in which some sodium cations of the hectorite clay have been replaced by organic groups, include, but are not limited to Bentone 27VCG—stearalkonium hectorite having the formula of $[Na,((CH_3)_2N(CH_2)_{18} CH_3)(CH_2C_6H_5))]_{0.33}$ $[Mg_{2.67}Li_{0.33}]Si_4O_{10}(OH)_2$ and disteardimonium hectorite having the formula of $[Na,((CH_3)_2 N((CH_2)_{17}CH_3)_2N((CH_2)_{17}(CH_3)_2)]_{0.33}[Mg_{2.67}Li_{0.33}] Si_4O_{10}(OH)_2$. In an embodiment, the layered silicate clay may include one or more of a sodium calcium aluminum magnesium silicate clay, a lithium magnesium sodium silicate clay, a sodium magnesium fluorosilicate clay, and an organo-modified hectorite clay. In another embodiment, the layered silicate clay may be a synthetic smectite clay, such as a laponite clay.

The layered silicate clay may be present in an amount of 0.5 to 5 weight %, or 1 to 5 weight %, or 2 to 5 weight %, based on the total weight of the antiperspirant/deodorant composition.

In an embodiment, the acyl substituted polyvinylpyrrolidone may include an acyl substituted polyvinylpyrrolidone having an average acyl chain length of 16 to 30 carbon atoms or 18 to 30 may include or may be an acyl substituted polyvinylpyrrolidone having an acyl chain length of 30 carbon atoms. In another embodiment, the acyl substituted polyvinylpyrrolidone may be present in an amount of 0 to 1 weight %, or 0.05 to 1 weight %, or 0.05 to 0.5 weight %, based on the total weight of the composition.

Non limiting examples of commercially available acyl substituted polyvinylpyrrolidone (PVP) include Triacontanyl PVP having an acyl chain length of 30 carbon atoms as Unimer U-6; VP/Eicosene Copolymer having an acyl chain length of 20 carbon atoms as Unimer U-15; VP/Hexadecene Copolymer having an acyl chain length of 16 carbon atoms as Unimer U-151; VP/Hexadecende Copolymer, Octyldodecanol having an average acyl chain length of 19 carbon atoms as Unimer U-1946, all available from Induchem USA Inc. of New York, N.Y.

Additionally, a Triacontanyl PVP can also be obtained from Ashland Specialty Ingredients with the trade name Ganex™ WP-660 and as Vida-Care AVP-30 from Lanbson Ltd of West Yorkshire UK; VP/Eicosene Copolymer as Vida-Care AVP-20; and VP/Hexadecene Copolymer Vida-Care AVP-16 from Lanbson Ltd of West Yorkshire UK.

In one embodiment of the antiperspirant/deodorant compositions of the present disclosure, the clay and acyl substituted polyvinylpyrrolidone may be present in a mass ratio of 0.1:1 to 1:0.1.

In an embodiment, the antiperspirant/deodorant compositions of the present disclosure may be essentially free of alkyl olefinic acid amide/olefinic acid or ester copolymer, such as octylacrylamide or propenamide/acrylates copolymer.

In another embodiment, the antiperspirant/deodorant compositions of the present disclosure may be essentially free of aluminum-based antiperspirant active.

Carrier

The carrier present in the antiperspirant/deodorant compositions of the present disclosure may include a polyhydric alcohol or may be a mixture of a polyhydric alcohol and water. In one embodiment, the polyhydric alcohol present in the antiperspirant/deodorant compositions of the present disclosure may include one or more organic compounds which contain about 2 to about 6 carbon atoms and about 2 to about 6 hydroxy groups. Suitable polyhydric alcohols include, but are not limited to, ethylene glycol, propylene glycol, 1,3-propanediol, trimethylene glycol, butylene glycol, diethylene glycol, dipropylene glycol, glycerin, sorbitol, xylitol and mixtures thereof. In one embodiment, the polyhydric alcohol may be propylene glycol or dipropylene glycol or a mixture thereof. In an embodiment, the polyhydric alcohol may include or may be propylene glycol. The polyhydric alcohol can be present in any suitable amount in the antiperspirant/deodorant compositions of the present disclosure, such as in the range from 70 to 98 weight %, or 72 to 93 weight %, based on the total weight of the antiperspirant/deodorant composition.

In an embodiment, water may be added in an amount of 0.1 to 20 weight %, based on the total weight of the antiperspirant/deodorant composition.

Thickening Agent

The antiperspirant/deodorant compositions of the present disclosure may include a saturated and/or an unsaturated $C_{14-22}$ fatty acid salt, which may be an alkali metal, an alkaline earth metal, transition metal, or an amine salts of $C_{14-22}$ fatty acid. Suitable examples of $C_{14-22}$ fatty acid include, but are not limited to myristic, palmitic, stearic, arachidic, behenic, oleic, linoleic, linolenic acid and mixtures thereof. In another embodiment, the $C_{14-22}$ fatty acid salt may include one or more counterions chosen from sodium, potassium, calcium, magnesium, zinc, diethylamine, triethyl amine and mixtures thereof. In another embodiment, the $C_{14-22}$ fatty acid salt may be chosen from sodium stearate, potassium stearate, magnesium stearate, aluminum monostearate, sodium oleate, sodium palmitate, sodium behenate, diethylamine stearate, triethylamine stearate, triethylemine oleate, and mixtures thereof. In one embodiment, the $C_{14\text{-}22}$ fatty acid salt may be present in an amount of 0 to 8 weight %, or 3 to 7 weight %, or 5 to 7 weight %, based on the total weight of the antiperspirant/deodorant composition.

One purpose of the $C_{14\text{-}22}$ fatty acid salts is to thicken the antiperspirant/deodorant composition so that it functions as a "stick-type" deodorant. As such, the $C_{14\text{-}22}$ fatty acid salts may be referred to herein as a thickening agent, a gelling agent or a structurant.

In one embodiment, the antiperspirant/deodorant compositions of the present disclosure may include an ester of glycerin and a $C_{10\text{-}18}$ fatty acid. The $C_{10\text{-}18}$ fatty acid may be chosen from caprylic, capric, lauric, myristic, palmitic, stearic, oleic, linoleic, and linolenic acids and mixtures thereof. In one embodiment, the $C_{10\text{-}18}$ fatty acid ester may be present in the compositions of the present disclosure in an amount of 0 to 0.8 weight %, or 0.2 to 0.7 weight %, or 0.3 to 0.6 weight %, based on the total weight of the antiperspirant/deodorant composition.

Other Optional Ingredients

The antiperspirant/deodorant compositions of the present disclosure may also include other ingredients. For example, the antiperspirant/deodorant compositions of the present disclosure may include one or more ingredients for achieving and maintaining a desired consistency, one or more ingredients for giving the product a soothing skin feel, one or more antioxidants, one or more fragrances and one or more ingredients for fragrance duration or retention, additional deodorizing agent, and clarifier-surfactant. Some ingredients listed herein can provide more than one function to the compositions. For example, certain emollients can act as lipophilic carrier material and a gelling agent at the same time.

Non-limiting examples of ingredients suitable for use in achieving and maintaining desired consistency are, for example, caprylic capric triglyceride, capryl glycol, glycerin, and glyceryl laurate.

Non-limiting examples of ingredients suitable for use as skin soothing agents are, for example, aloe vera leaf extract or juice, chamomile aqueous extract, other herbal extracts and oatmeal. Non-limiting examples astringents include, for example witch hazel water. The present antiperspirant/deodorant compositions may include one or more of aloe vera leaf extract or juice present in an amount of 0.5 to 10 weight %, witch hazel (also known as witch hazel water) present in an amount of 1 to 10 weight %, and chamomile aqueous extract present in an amount of 1 to 20 weight %, based on the total weight of the antiperspirant/deodorant composition.

Non-limiting examples of ingredients suitable for use as antioxidants are, for example, one or more of tocopherol and its derivatives, butyl hydroxyanisole (BHA), butyl hydroxytoluene (BHT), erythorbic acid, propyl gallate, sodium erythorbate, tertiary butyl hydroquinone (TBHQ), rosemary extract and, more preferably, ascorbic acid and salts thereof. The antioxidant compound may be one or more of tocopherol and its derivatives present in an amount of 0.001 to 0.5 weight %, or butyl hydroxyanisole (BHA) present in an amount of 0.0075 to 0.1 weight %, butyl hydroxytoluene (BHT) present in an amount of 0.005 to 0.02 weight %, erythorbic acid present in an amount of 0.05 to 1 weight %, propyl gallate present in an amount of 0.01 to 1 weight %, sodium erythorbate present in an amount of 0.05 to 1 weight %, tertiary butyl hydroquinone (TBHQ) present in an amount of 0.005 to 0.1 weight %, rosemary extract present in an amount of 0.02 to 0.4 weight %, and ascorbic acid and salts thereof present in an amount of 0.01 to 0.1 weight %, based on the total weight of the antiperspirant/deodorant composition.

The antiperspirant/deodorant compositions of the present disclosure may include natural and synthetic fragrance(s), if a scented product is desired. Fragrances can be used in any suitable amount, such as in the range of 0.01 to 3%, and, for example, at a level of about 1%.

The antiperspirant/deodorant compositions of the present disclosure may also include ingredients suitable for use for fragrance duration or longevity, such as, for example silica shells, polymeric, or other encapsulates compatible with antiperspirant/deodorant base formulation.

The antiperspirant/deodorant compositions of the present disclosure may include additional deodorizing compounds, for example, including but not limited to, capryl glycol, glyceryl laurate, capric triglyceride, present in an amount of 0.1 to 4 weight %, and lemongrass oil present in an amount of 0.01 to 0.1 weight %, based on the total weight of the antiperspirant/deodorant composition.

The antiperspirant/deodorant compositions of the present disclosure may include a clarifier-surfactant, including, but not limited to, pentadoxynol-200, tetra(hydroxypropyl)diamine, 2-amino-2-methylpropanol, 2-amino-2-hydroxymethyl-1,3-propanediol, poly($C_{2\text{-}4}$ alkylene) glycol ethers of $C_{12\text{-}22}$ fatty alcohols in which the polyalkylene glycol portion contains from about 10 to about 100 alkyleneoxide repeating units. In an embodiment, the clarifier-surfactant may include from among laureth-10, laureth-20, laureth-30. laureth-40, PEG-10 Myristyl Ether, steareth-10, steareth-20, steareth-40, steareth-100, PEG-50 Stearyl Ether, steareth-100, beheneth-20 and mixtures thereof. In another embodiment, the clarifier-surfactant may include or may be polyoxyethylene 3-pentadecyl phenyl ether. The clarifier-surfactant may be present in the antiperspirant/deodorant compositions of the present disclosure in an amount of 2 to 3.5 weight %, based on the total weight of the antiperspirant/deodorant composition.

Additional gelling agent(s) such as, fatty alcohols may be incorporated into the antiperspirant/deodorant compositions of the present disclosure. In one embodiment, the fatty alcohol may be stearyl alcohol or docosyl alcohol (behenyl alcohol).

In one embodiment, the antiperspirant/deodorant compositions of the present disclosure have an appearance consistent with the product appearing clear, essentially clear, or non-visible when applied to the user's body. In this regard, the antiperspirant/deodorant compositions of the present disclosure may appear opaque, turbid, or colored when formed into a shape consistent with a final antiperspirant/deodorant product (e.g., shapes know in the art as used for stick-type deodorants) as long as the product is clear, essentially clear, or non-visible when applied to the user's body in amounts consistent with typical use. A definition of clear is that it is not highly visible after application and equilibration in the underarm.

The antiperspirant/deodorant compositions according to the present disclosure can be packaged in conventional containers, using conventional techniques. For example, where the composition may be a stick composition, the composition, while still in liquid form, can be introduced into a dispensing package as conventionally done in the art, and cooled therein so as to thicken in the package. Thereafter, the product can be dispensed from the dispensing package as conventionally done in the art, to deposit the active material, for example, on the skin. This provides good deposition of the active material on the skin. Other methods of producing a final antiperspirant/deodorant product may include those taught in U.S. Pat. No. 7,128,901 to Jonas, et al., wherein the product may be formed into a stick-like shape without the heating/melting step typical of these processes, or reasonable variations thereof. The antiperspirant/deodorant compositions according to the present disclosure may be in the form of cream, or flowable gel instead of stick form and may be dispensed through appropriate packaging such as roll-ons, tubes, or gels containers.

The antiperspirant/deodorant compositions of the present disclosure may be applied to the skin, such as an axillary area of a person using conventional techniques suitable for stick, cream, or flowable gel, and in a manner that would result in typical loading as used for underarm products. For example, for use as an antiperspirant/deodorant composition, the loading can be in an amount of 0.5 to 10 mg/cm$^2$, or 2 to 9 mg/cm$^2$, or 5 mg/cm$^2$.

The antiperspirant/deodorant compositions of the present disclosure provide several advantages over conventional antiperspirant/deodorant compositions. First and foremost is that the antiperspirant/deodorant compositions are free of aluminum, as aluminum has been perceived to have adverse side effects in some people. Secondly, the antiperspirant/deodorant compositions as disclosed hereinabove may provide underarm protection by providing moisture barrier and thereby reduced apparent perspiration for longer time. Furthermore, the antiperspirant/deodorant compositions of the present disclosure not including zinc oxide as an antiperspirant and $C_{1-5}$ monohydric alcohols, may provide reduced skin stinging partly due to the absence of $C_{1-5}$ monohydric alcohols and/or irritation potential, and perceived health related issues.

Methods of Reducing Apparent Perspiration

In an aspect, there may be a method of reducing apparent perspiration including applying the antiperspirant/deodorant composition, as disclosed hereinabove, to an axillary area of a person, wherein the antiperspirant active in combination with a fatty acid salt forms a hydrophobic film on the axillary area of the person, thereby acting as moisture barrier and reducing apparent perspiration. Without wishing to be bound by theory, it is believed that the addition of the acyl substituted polyvinylpyrrolidone including an acyl chain length having 16 to 30 carbon atoms may enhance the antiperspirant effect by providing an additional hydrophobic film.

In an embodiment of the method, the antiperspirant active may include both an acyl substituted polyvinylpyrrolidone and a clay and the fatty acid salt may include a completely or partially neutralized stearic acid.

In another aspect, there may be a use of a combination of an antiperspirant active and a fatty acid salt to reduce apparent perspiration when applied to an axillary area of an armpit, the antiperspirant active including a layered silicate clay and/or an acyl substituted polyvinylpyrrolidone. For such uses, the combination of an antiperspirant active and a fatty acid salt may be present in a mixture of a polyhydric alcohol and water to form an antiperspirant/deodorant composition in the stick, cream or flowable gel form. The fatty acid salt may be chosen from an alkali metal, an alkaline earth metal, a transition metal, or an amine salt of $C_{14-22}$ fatty acids. The polyhydric alcohol may be selected from among organic compounds containing about 2 to about 6 carbon atoms and about 2 to about 6 hydroxy groups. The disclosed antiperspirant/deodorant stick composition may be free of metal salt based antiperspirant actives, such as aluminum-based antiperspirant actives, and also free of $C_{1-5}$ monohydric alcohol chosen from ethyl alcohol, isopropyl alcohol, n-propanol, n-butanol, sec. butanol, isobutanol, pentanol, and mixtures thereof.

The antiperspirant/deodorant composition of the present disclosure provides an increase in resistance to hydrostatic pressure observed in sweat ducts in an amount of at least 10% or at least 20% or at least 40%, as measured by the method disclosed hereinbelow, as compared to resistance to hydrostatic pressure provided by a comparative antiperspirant/deodorant composition having an identical composition as that of the antiperspirant/deodorant composition of the present disclosure, except that the comparative antiperspirant/deodorant compositiadvantages on has either a layered silicate clay or an acyl substituted polyvinylpyrrolidone having an acyl chain length ranging from 16 to 30 carbon atoms, as an antiperspirant active. In an embodiment, the acyl substituted polyvinylpyrrolidone has the acyl chain length of 30 carbon atoms. In another embodiment, the layered silicate clay may be a synthetic or natural lithium magnesium sodium silicate clay.

The antiperspirant/deodorant composition of the present disclosure when applied on a skin surface provides a reduction in sweat/perspiration in an amount of at least 10%, or at least 15%, or at least 20%, as measured by the method disclosed hereinbelow, and in comparison to a skin surface without treatment with any antiperspirant/deodorant composition (i.e. untreated skin surface). In certain embodiments, the application may be to axilla.

The examples and other embodiments described herein are exemplary and not intended to be limiting in describing the full scope of compositions and methods of this disclosure. Equivalent changes, modifications and variations of specific embodiments, materials, compositions and methods may be made within the scope of the present disclosure, with substantially similar results.

Examples

Test Method

Resistance to Hydrostatic Pressure:

Resistance of films of antiperspirant/deodorant composition of the present disclosure to hydrostatic pressure due to that would be experienced at the outlet of a sweat duct was determined in a simulated environment using a filter treated with the antiperspirant/deodorant composition and measuring the permeation coefficient of the coated filter for salt water, typically 0.1 M NaCl. The permeation coefficient (κ) can be determined using Darcy's law, which provides a relationship between the instantaneous discharge rate (Q) through a porous medium, the viscosity of the fluid (η) and the pressure drop (ΔP) over a given distance (L):

$$\kappa_i = (Q_i \cdot \eta \cdot L)/(A \cdot \Delta P_i) \quad (1)$$

Where:
κ=Permeation Coefficient for Volume i (units, e.g., μD or darcy unit))
$Q_i$=Flow Rate for Volume i (units of volume per time, e.g., m$^3$/s)
η=Fluid Viscosity ((units of viscosity, e.g., Pa·s)
L=Filter+Sample Thickness (units of length, e.g., m)
A=Cross Sectional Area of Flow (units of area, e.g., m$^2$)
$\Delta P_i$=Pressure Drop Across Filter for Volume i (units of pressure, e.g., pascals)

The darcy unit is referenced to a mixture of unit systems. A porous medium with a permeability of 1 darcy permits a flow of 1 cm³/s of a fluid with viscosity 1 cP (1 mPa·s) under a pressure gradient of 1 atm/cm acting across an area of 1 cm². A millidarcy (md) is equal to 0.001 darcy and a microdarcy (μd) equals 0.000001 darcy.

As can be seen from equation (1), a reduction in the permeation coefficient reflects enhanced resistance to hydrostatic pressure. Increased resistance to hydrostatic pressure is expected to be consistent with an increase in antiperspirant benefits due to plug formation or superficial blockage in the sweat ducts.

Essentially a known amount of antiperspirant/deodorant composition of the present disclosure was spread evenly onto a cellulosic filter with a 20 μm equivalent pore size. The filters with treated side up were equilibrated for approximately 15 hours over filters saturated with 1 M NaCl. The filters were then removed, allowed to air dry, then filtered with treated side down using negative pressure to simulate the hydrostatic pressures observed in and at the surface of a sweat duct. The permeation coefficient was then measured in an experimental design as a function of acyl chain length, amount of stearic acid, clay, and acyl substituted polyvinylpyrrolidone or other experimental variables.

Antiperspirant Efficacy by Measurement of Sweat Reduction

A balanced block design was used to evaluate n different antiperspirant/deodorant compositions (product) with n≤11, and an untreated control (U) using (n+1) sites on the back of approximately 30 panelists. The n products and the untreated control were randomly assigned to the (n+1) sites following a randomization code, such that an equal number of products were assigned to each of the (n+1) possible locations. The inclusion of an untreated control allowed paired comparisons of each active product and the untreated control. Products were assigned to each site after ranking the panelists in order of highest to lowest sweat output at baseline (mean of the (n+1) sites) following the randomization code. Sweat amounts were measured gravimetrically by weighing Webril pads before and after sweating and obtaining the weight difference due to absorbed sweat.

An analysis of covariance (ANCOVA) model was used to compare percent change from baseline untreated control site. The logarithm of the sweat production was the dependent variable in the model and the independent wolfs included panelists, log baseline sweat output, location on the back, treatment composition (product). The model used herein for analysis was an extension of the SSEM model proposed by Levine and Murphy (Murphy T D and Levine M J: Analysis of Antiperspirant Efficacy Test Results, J. Soc. Cosmet. Chem., 42, 167-197, May-June 1991), The use of this statistical model would be obvious to one of ordinary skilled in the art.

% Sweat Reduction was calculated using following equation:

$$\% \text{ Sweat Reduction} = 100 \times \left[1 - \frac{\text{Amount of sweat from treated site}}{\text{Amount of sweat from untreated control site}}\right]$$

Example 1 & Comparative Examples A and B:
Antiperspirant/Deodorant Compositions Including Varying Amounts of Stearic Acid, Triacontanyl PVP, and Laponite XLG Various antiperspirant/deodorant compositions shown in Table 1 were prepared as follows:

Weighed propylene glycol into a beaker and heated to 75° C. while mixing using a high shear mixing blade. While maintaining the temperature at 75° C., added stearic acid to the propylene glycol with continuous mixing at 500 rpm until completely dissolved, followed by dropwise addition of caustic (50% NaOH) while maintaining the temperature constant and continuous mixing at 500 rpm until completely dissolved. After compete dissolution of caustic, added the Triacontanyl PVP having an acyl chain length of 30 carbon atoms) until completely dissolved, followed by slow addition of clay such as laponite-XLG (lithium magnesium sodium silicate clay), while still maintaining the temperature at 75° C. with continuous mixing at 1000 rpm until the clay is completely dispersed. Added water, if used, while maintaining the temperature of the formulation at 75° C. with continuous mixing at 1000 rpm. Once water is completely dissolved, turned off the heat to allow the antiperspirant/deodorant formulation to cool off to approximately 60° C., while adjusting the mixing speed as necessary. Transferred the antiperspirant/deodorant formulation into a labeled sample collection jar and periodically shaking the jar for approximately 15 30 seconds to insure uniformity within the sample, as the cooling process continued and until the sample solidified.

Permeation coefficient was then determined for these antiperspirant/deodorant compositions using the procedure described above. The antiperspirant/deodorant compositions and the permeation results are also summarized in Table 1.

TABLE 1

Effect of the presence of Triacontanyl PVP and lithium magnesium sodium silicate clay in antiperspirant/deodorant compositions on the permeation coefficient

| Sample # | weight % Propylene Glycol | weight % Stearic Acid | weight % Caustic (50% NaOH) | weight % H₂O | weight % Triacontanyl PVP having C30 acyl chain length | weight % Laponite XLG (lithium magnesium sodium silicate clay) | Mean $\kappa_{n,o}$ (uDarcy) | % change in $\kappa_{n,o}$ (uDarcy) | p ≤ 0.05 |
|---|---|---|---|---|---|---|---|---|---|
| Comparative A | 78.02 | 3.37 | 0.94 | 17.68 | 0 | 0 | 0.1467 | — | A |
| Example 1.1 | 77.35 | 3.37 | 0.94 | 17.68 | 0 | 0.67 | 0.0828 | 44% | B |
| Example 1.2 | 77.54 | 3.37 | 0.94 | 17.68 | 0.1 | 0.38 | 0.0970 | 34% | B |
| Example 1.3 | 77.45 | 3.37 | 0.94 | 17.68 | 0.19 | 0.38 | 0.0391 | 73% | C |
| Example 1.4 | 77.64 | 3.37 | 0.94 | 17.68 | 0.38 | 0 | 0.0465 | 68% | C |
| Example 1.5 | 76.97 | 3.37 | 0.94 | 17.68 | 0.38 | 0.67 | 0.0066 | 96% | D |
| Comparative B | 73.71 | 6.74 | 1.87 | 17.68 | 0 | 0 | 0.0118 | — | D |
| Example 1.6 | 73.04 | 6.74 | 1.87 | 17.68 | 0 | 0.67 | 0.0099 | 16% | D |

TABLE 1-continued

Effect of the presence of Triacontanyl PVP and lithium magnesium sodium silicate clay in antiperspirant/deodorant compositions on the permeation coefficient

| Sample # | weight % Propylene Glycol | weight % Stearic Acid | weight % Caustic (50% NaOH) | weight % H$_2$O | weight % Triacontanyl PVP having C30 acyl chain length | weight % Laponite XLG (lithium magnesium sodium silicate clay) | Mean $\kappa_{n,o}$ (uDarcy) | % change in $\kappa_{n,o}$ (uDarcy) | p ≤ 0.05 |
|---|---|---|---|---|---|---|---|---|---|
| Example 1.7 | 73.24 | 6.74 | 1.87 | 17.68 | 0.1 | 0.38 | 0.0142 | −20% | D |
| Example 1.8 | 73.14 | 6.74 | 1.87 | 17.68 | 0.19 | 0.38 | 0.0177 | −50% | D |
| Example 1.9 | 73.33 | 6.74 | 1.87 | 17.68 | 0.38 | 0 | 0.0119 | −1% | D |
| Example 1.10 | 72.66 | 6.74 | 1.87 | 17.68 | 0.38 | 0.67 | 0.0069 | 41% | D |

In Table 1, the % change in permeability coefficient, $\kappa_{n,o}$ of Examples 1.1 to 1.5 were calculated with respect to the Comparative Example A and that of Examples 1.6 to 1.10 with respect to the Comparative Example B.

Table 1 shows that in antiperspirant/deodorant compositions including 3.37 weight % of stearic acid, that presence of either Laponite XLG (Example 1.1) or Triacontanyl PVP 3.6 (Example 1.4) results in a decrease in permeation coefficient by 44% or 68% as compared to Comparative Example A without any antiperspirant active. Furthermore, comparing Comparative Example A with B shows that upon increasing the amount of stearic acid from 3.37 to 6.74 weight %, in absence of an antiperspirant active, there was a decrease in permeation coefficient. However, comparing Example 1.5 with Comparative Example A and Example 1.10 with Comparative Example A, it should be noted that smallest permeation coefficient (0.0066 µDarcy) can be obtained by the presence of both Triacontanyl PVP and Laponite XLG with only 3.37 weight % of stearic acid. Thus, one can tune the amount of stearic acid, Triacontanyl PVP and Laponite XLG to arrive at the desired antiperspirant/deodorant composition having the desired hardness.

Multivariant ANOVA analysis ($\kappa_{n,o}$ vs weight % Stearic Acid, weight % Triacontanyl PVP, and weight % Laponite XLG) showed that:
 (i) $\kappa_{n,o}$ is highly dependent on all three variables (p<0.0001), i.e. amount of stearic acid, Triacontanyl PVP, and Laponite XLG.
 (ii) There are cross interactions between the Stearic Acid and the Laponite XLG and also between the Triacontanyl PVP and Laponite XLG.
 (iii) A statistically significant change in $\kappa_{n,o}$ (p<0.05) can be detected when stearic acid changes by more than about 0.78 weight %, Triacontanyl PVP changes by 0.103 weight %, and Laponite XLG by 0.304 weight %.

Example 2: Antiperspirant efficacy by Measurement of Sweat Reduction of Antiperspirant/Deodorant Compositions Including Varying Amounts of Stearic Acid, Triacontanyl PVP and Laponite XLG Four antiperspirant/deodorant compositions were made with varying amounts of Triacontanyl PVP and laponite-XLG, using the procedure described for Example 1, except that no water was added other than the water present in caustic solution and water of hydration present in various ingredients.

Antiperspirant efficacy of these antiperspirant/deodorant compositions was determined by measuring % sweat reduction using the procedure described hereinabove. The antiperspirant/deodorant compositions and the sweat reduction results are also summarized in Table 2.

TABLE 2

% Sweat reduction based on sweat weight vs control untreated sites.

| | Propylene Glycol | Caustic (50%), weight % | Stearic Acid, weight % | Triacontanyl PVP, weight % | Laponite XLG, weight % | % Sweat Reduction vs Untreated |
|---|---|---|---|---|---|---|
| Example 2.1 | QS | 1.87 | 6.74 | 0 | 0.7 | 21.2 |
| Example 2.2 | QS | 1.87 | 6.74 | 0.2 | 0.35 | 22.0 |
| Example 2.3 | QS | 1.87 | 6.74 | 0.4 | 0.7 | 25.5 |
| Example 2.4 | QS | 1.87 | 6.74 | 0.4 | 0 | 25.4 |

Table 2 shows that the antiperspirant/deodorant compositions of the present disclosure in a stearate glycol based stick form including Laponite XLG clay and/or Triacontanyl PVP polymer deliver sweat reduction in an amount of 20% or more in treated sites as compared to the untreated sites using the method outlined above. Without wishing to be bound by theory, Table 2 shows that the presence of acyl substituted polyvinylpyrrolidone, such as triacontanyl PVP having C30 acyl chain length improves the antiperspirant efficacy of the antiperspirant/deodorant compositions including Laponite XLG clay.

Example 3: Effect of Acyl Chain Length of Acyl Substituted Polyvinylpyrrolidone on the Permeation Coefficient of Antiperspirant/Deodorant Compositions Four antiperspirant/deodorant compositions were made with different acyl substituted polyvinylpyrrolidone, having different acyl chain length, using the procedure described for Example 1, except that no clay and no water was added other than the water present in the caustic solution and water of hydration present in various ingredients.

Triacontanyl PVP having an acyl chain length of 30 carbon atoms, VP/Eicosene Copolymer having an acyl chain length of 20 carbon atoms, VP/Hexadecene Copolymer having an acyl chain length of 16 carbon atoms, VP/Hexadecene Copolymer, Octyldodecanol, having an acyl chain length of 19 carbon atoms) were used. Table 3 summarizes the composition and results of permeation coefficient measured using the procedure disclosed hereinabove.

TABLE 3

Effect of acyl chain length of acyl substituted polyvinylpyrrolidone (PVP) on the Permeation Coefficient

| Acyl substituted polyvinylpyrrolidone | # of carbon atoms in the acyl group of the acyl substituted PVP | Acyl substituted PVP, weight % | Stearic Acid, weight % | Caustic (50%), weight % | Propylene Glycol, weight % | Permeation coefficient, $\kappa$ of samples of $\kappa_{o,n}$ (uDarcy) |
|---|---|---|---|---|---|---|
| VP/Hexadecene Copolymer | 16 | 3 | 6.74 | 1.87 | QS | 0.0045 |
| VP/Hexadecene Copolymer, Octyldodecanol | 19 | 3 | 6.74 | 1.87 | QS | 0.0023 |
| Eicosene Copolymer | 20 | 3 | 6.74 | 1.87 | QS | 0.0031 |
| Triacontanyl PVP | 30 | 3 | 6.74 | 1.87 | QS | 0.0046 |
| None | N/A | 0 | 6.74 | 1.87 | QS | 0.0052 |

Table 3 shows that the acyl substituted polyvinylpyrrolidone with various acyl chain lengths, such as with carbon atoms from 16 to 30 when present in the antiperspirant/deodorant compositions of the present disclosure having no clay, provide a reduction in permeation coefficient, which in turn reflects enhanced resistance to hydrostatic pressure. Increased resistance to hydrostatic pressure is expected to be consistent with an increase in antiperspirant benefits due to plug formation or superficial blockage in the sweat ducts.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. An antiperspirant/deodorant composition comprising:
a carrier comprising a polyhydric alcohol or a mixture of a polyhydric alcohol and water, wherein the polyhydric alcohol comprises an organic compound containing 2 to 6 carbon atoms and 2 to 6 hydroxy groups;
a thickening agent comprising a C14-22 fatty acid salt, wherein the C14-22 fatty acid salt comprises at least one of an alkali metal, an alkaline earth metal, a transition metal, or an amine salt of C14-22 fatty acid; and
an antiperspirant active consisting essentially of one or more of a layered silicate clay and an acyl substituted polyvinylpyrrolidone having an acyl chain length ranging from 16 to 30 carbon atoms,
wherein the antiperspirant/deodorant composition is essentially free of a C1-5 monohydric alcohol and essentially free of a metal salt based antiperspirant active.

2. The antiperspirant/deodorant composition of claim 1, wherein the layered silicate clay comprises one or more of a sodium calcium aluminum magnesium silicate clay, a lithium magnesium sodium silicate clay, a sodium magnesium fluorosilicate clay, and an organo-modified hectorite clay.

3. The antiperspirant/deodorant composition of claim 1, wherein the C14-22 fatty acid salt comprises at least one of myristic, palmitic, stearic, behenic, oleic, linoleic, and linolenic acid, and one or more of sodium, potassium, calcium, magnesium, zinc, diethylamine, triethyl amine as a counterion.

4. The antiperspirant/deodorant composition of claim 1, wherein the C14-22 fatty acid salt comprises a completely or a partially neutralized stearic acid.

5. The antiperspirant/deodorant composition of claim 1, wherein the acyl substituted polyvinylpyrrolidone has the acyl chain length of 30 carbon atoms.

6. The antiperspirant/deodorant composition of claim 1, wherein the polyhydric alcohol is propylene glycol.

7. The antiperspirant/deodorant composition of claim 1, wherein the polyhydric alcohol is present in an amount of 65 to 95 weight %, based on the total weight of the antiperspirant/deodorant composition.

8. The antiperspirant/deodorant composition of claim 1, wherein water is present in an amount of 0.1 to 20 weight %, based on the total weight of the antiperspirant/deodorant composition.

9. The antiperspirant/deodorant composition of claim 1, wherein the C14-22 fatty acid salt is present in an amount of 0.5 to 8 weight %, based on the total weight of the antiperspirant/deodorant composition.

10. The antiperspirant/deodorant composition of claim 1, wherein the antiperspirant active comprises clay present in an amount of 0.5 to 5 weight %, based on the total weight of the antiperspirant/deodorant composition.

11. The antiperspirant/deodorant composition of claim 1, wherein the antiperspirant/deodorant composition is an antiperspirant/deodorant stick composition, an antiperspirant/deodorant cream composition, or an antiperspirant/deodorant flowable gel composition.

* * * * *

UNITED STATES PATENT AND TRADEMARK OFFICE
CERTIFICATE OF CORRECTION

PATENT NO. : 11,147,755 B2
APPLICATION NO. : 16/468778
DATED : October 19, 2021
INVENTOR(S) : Hilliard, Jr. et al.

Page 1 of 1

It is certified that error appears in the above-identified patent and that said Letters Patent is hereby corrected as shown below:

In the Specification

In Column 11, Line 43, delete "wolfs" and insert -- terms --, therefor.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*